United States Patent
Nuta et al.

(10) Patent No.: US 12,048,582 B2
(45) Date of Patent: Jul. 30, 2024

(54) METHOD AND DEVICE FOR LOCALIZING A VEIN WITHIN A LIMB

(71) Applicant: THERACLION SA, Malakoff (FR)

(72) Inventors: Michel Nuta, Gentilly (FR); Jérémie Anquez, Paris (FR); Anthony Grisey, Saint Cyr l'Ecole (FR)

(73) Assignee: Theraclion SA, Malakoff (FR)

( * ) Notice: Subject to any disclaimer, the term of this patent is extended or adjusted under 35 U.S.C. 154(b) by 199 days.

(21) Appl. No.: 17/046,461

(22) PCT Filed: Mar. 15, 2019

(86) PCT No.: PCT/EP2019/056570
§ 371 (c)(1),
(2) Date: Oct. 9, 2020

(87) PCT Pub. No.: WO2019/201522
PCT Pub. Date: Oct. 24, 2019

(65) Prior Publication Data
US 2021/0153839 A1 May 27, 2021

(30) Foreign Application Priority Data
Apr. 20, 2018 (EP) .................................... 18315008

(51) Int. Cl.
*A61B 8/08* (2006.01)
*A61B 8/00* (2006.01)
*A61B 8/06* (2006.01)

(52) U.S. Cl.
CPC ................ *A61B 8/085* (2013.01); *A61B 8/06* (2013.01); *A61B 8/0891* (2013.01);
(Continued)

(58) Field of Classification Search
CPC ......... A61B 8/085; A61B 8/06; A61B 8/0891; A61B 8/4209; A61B 8/4461; A61B 8/488;
(Continued)

(56) References Cited

U.S. PATENT DOCUMENTS

| 3,527,197 A | 9/1970 | Ware et al. |
| 6,231,507 B1 | 5/2001 | Zikorus et al. |

(Continued)

FOREIGN PATENT DOCUMENTS

| JP | 2003504103 A | 2/2003 |
| JP | 2007000218 A | 1/2007 |

(Continued)

OTHER PUBLICATIONS

Bechsgaard Thor et al: "Blood flow velocity in the popliteal vein using transverse oscillation ultrasound", Progress in Biomedical Optics and Imaging, SPIE—International Society for Optical Engineering, Bellingham, WA, US , vol. 9790, Apr. 1, 2016 (Apr. 1, 2016), pp. 979003-979003. (Year: 2016).*

(Continued)

*Primary Examiner* — Baisakhi Roy
*Assistant Examiner* — Kaitlyn E Sebastian
(74) *Attorney, Agent, or Firm* — Finch & Maloney PLLC

(57) ABSTRACT

A method of localizing and preferably visualizing a vein within a limb, preferably within a leg, of a patient, with an imaging device. The method includes the following steps of: fully or partially collapsing at least a segment of the vein to be localized at a collapsing site during a collapsing step; inducing blood flow within the vein at the collapsing site, while the segment of the vein is fully or partially collapsed, during a pumping step; and visualizing the collapsing site with the imaging device in an imaging step, at least during the pumping step.

11 Claims, 3 Drawing Sheets

Figure 1:
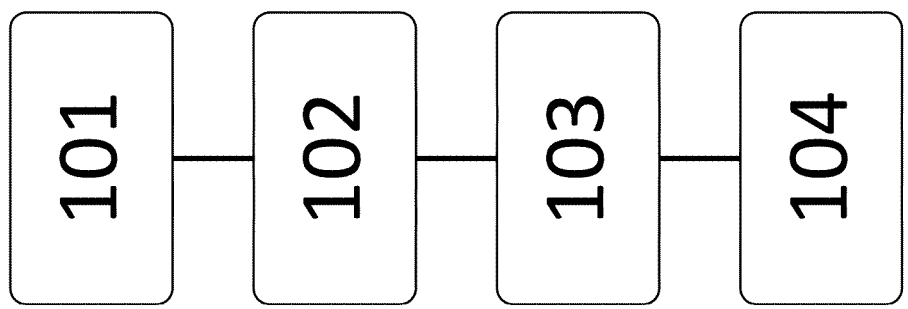

(52) U.S. Cl.
CPC .......... *A61B 8/4209* (2013.01); *A61B 8/4461* (2013.01); *A61B 8/488* (2013.01); *A61B 8/54* (2013.01)

(58) Field of Classification Search
CPC ..... A61B 8/54; A61B 34/30; A61B 2090/378; A61B 8/14; A61B 17/132; A61B 5/489; A61B 5/4836; A61B 5/704; A61B 8/403; A61N 7/02; A61N 2007/0052
See application file for complete search history.

(56) References Cited

U.S. PATENT DOCUMENTS

| | | | |
|---|---|---|---|
| 8,214,052 | B2 | 7/2012 | Merchant, Jr. |
| 2005/0049504 | A1 | 3/2005 | Lo et al. |
| 2007/0088346 | A1* | 4/2007 | Mirizzi ............... A61N 7/02 606/27 |
| 2007/0219448 | A1* | 9/2007 | Seip ................... A61N 7/02 600/453 |
| 2008/0306414 | A1 | 12/2008 | Petruzzello et al. |
| 2010/0191277 | A1* | 7/2010 | McEwen ........... A61B 17/1355 606/202 |
| 2011/0040188 | A1* | 2/2011 | Tamura ................ A61B 8/06 600/454 |
| 2014/0142615 | A1 | 5/2014 | Corrigan, Jr. |
| 2015/0201948 | A1 | 7/2015 | Kornowski et al. |
| 2021/0007716 | A1* | 1/2021 | Grisey ............... A61B 8/403 |

FOREIGN PATENT DOCUMENTS

| WO | WO-9855072 A2 * | 12/1998 | .......... A61B 17/135 |
|---|---|---|---|
| WO | 2006/129045 A2 | 12/2006 | |

OTHER PUBLICATIONS

Bartholomew, Sadie R. and Taney, John T: "Cost-Effective Engineering of a Small-Scale Bioreactor", Biotechnology and Bioengineering vol. 96, No. 2, Feb. 1, 2007 (Feb. 1, 2007), pp. 401-407, https://onlinelibrary.wiley.com/doi/pdf/10.1002/bit.21118 (Year: 2007).*

Thor Bechsgaard et al., Blood Flow Velocity in the Popliteal Vein Using Transverse Oscillation Ultrasound:, Progress in Biomedical Optics and Imaging, SPIE—International Society for Optical Engineering, Bellingham, WA, US, vol. 9790, Apr. 1, 2016, pp. 979003-979003 See European Search See International Search.

European Search Report Corresponding to 18315008.5 mailed Nov. 9, 2018.

International Search Report Corresponding to PCT/EP2019/056570 mailed Aug. 28, 2019.

Written Opinion Corresponding to PCT/EP2019/056570 mailed Aug. 28, 2019.

B. Meng, "Robotic Ultrasound Scanning for Deep Venous Thrombosis Detection Using RGB-D Sensor", 5th Annual IEEE International Conference on Cyber Technology in Automation, Control and Intelligent Systems, Jun. 8-12, 2015.

European Office Action Corresponding to 19709755.3 mailed Aug. 1, 2023.

Korean Office Action of corresponding application 10-2020-7032020 issued Feb. 21, 2024.

* cited by examiner

METHOD AND DEVICE FOR LOCALIZING A VEIN WITHIN A LIMB

The invention relates to a method and a device for localizing and visualizing a vein within a limb, preferably within a leg, of a patient, to a method for compressing a vein within a limb, preferably within a leg, of a patient and to a degassed liquid for use in tumescence of a vein of a patient according to the claims.

Heat treatments are used for the occlusion of veins, e.g. for the treatment of varicose veins.

U.S. Pat. No. 8,214,052 discloses an invasive method for treating a vein with a catheter which can be heated and therefore delivers heat to the vein wall. The catheter is positioned within the vein segment to be treated, is heated and withdrawn from the vein.

The main drawback of this method is that the catheter has to be invasively inserted in the vein segment to be treated, which carries a risk of perforation and is a complex process for tortuous veins.

HIFU devices, at the contrary, allow the non-invasive treatment of targets within a patient's body. For focusing the HIFU device within the target zone, imaging of the area surrounding the target zone is performed, e.g. by means of MRI or ultrasounds. In particular, HIFU devices with an integrated B-mode ultrasound imaging device, as described exemplarily in WO 2006/129045 A are used.

Since the occlusion of veins by coagulation of the vein wall relies on thermal effects, blood flow during treatment is not desired, since it cools down the treated vein wall. The vein segment to be treated has therefore to be collapsed in order to stop or at least substantially reduce the blood flow. Collapsing of the vein may be performed by means of a compression device, by elevating the limb of the patient, in the case of the leg in the so-called Trendelenburg position, and/or by tumescent anaesthesia. Since imaging of the target zone has to be performed when the vein has been collapsed in order to focus the HIFU device, the problem of clearly visualizing the vein segment to be treated arises.

If B-mode imaging is used, the collapsed vein is poorly visible. Also in the case of colour Doppler, the vein becomes invisible as soon as the blood flow is stopped. If blood flow is only reduced, colour Doppler may be helpful at the beginning of the heat treatment but, since vein wall coagulation induces shrinkage of the lumen, blood flow is even more reduced or stopped and the vein becomes invisible.

It is therefore aim of the present invention to provide a method for targeting and visualizing a vein within a limb which allows a reliable visualization of the at least partially collapsed vein and therefore enables focusing of a non-invasive thermal treatment device such as an HIFU device onto a target zone when the vein is collapsed.

This problem is solved with a method of localizing and preferably visualizing a vein within a limb, preferably within a leg, of a patient, with an imaging device according to the independent claims.

According to a first alternative of the method, the method comprises the following steps:

During a collapsing step, at least a segment of the vein to be localized is fully or partially collapsed at a collapsing site.

Collapsing of the vein is understood within the meaning of the present invention that the cross-section of the vein segment is reduced and/or the shape of the vein segment is changed.

Preferably, collapsing of the vein is performed by at least one of elevating at least the limb of the patient above a horizontal position, compressing the vein segment (e.g. with an inflatable balloon) and tumescence.

The limb, e.g. a leg, may be elevated in the so called "Trendelenburg position". Alternatively, the patient may lie on the side or on facing down on a table and the limb is raised. The table supporting a patient may be also inclined in order to raise the position of the limb, with the patient laying on the table supine, on the side or facing down.

In a pumping step, which is performed while the segment of the vein is fully or partially collapsed, a blood flow is induced into the collapsed vein segment at the collapsing site.

In addition, for immobilization of the limb and/or the patient, a vacuum mattress may be also used.

Preferably, during the pumping step, the vein is compressed and released at a compression site located near the collapsing site, preferably upstream of the collapsing site. Alternatively, other techniques such as for inducing a blood flow into the collapsed vein segment such as the Vasalva manoeuvre, or moving/asking the patient to move the toes or fingers, may be used.

Near the collapsing site is understood within the meaning of the present invention that the compression and releasing point is chosen such that blood flow can be forced to flow through the collapsed vein. In particular, the compression and releasing point is located at the most 50 cm from the collapsed segment of the vein. Preferably, the compression and releasing point is located within the same segment of the limb where the collapsed vein segment is located (e.g. thigh or calf).

In an imaging step, the collapsing site is imaged with the imaging device at least during the pumping step.

Preferably, the collapsing site is visualized on a display connected to the imaging device.

Since the collapsed segment of the vein becomes poorly visible when using known imaging devices, blood is forced to flow through the collapsed segment of the vein during the pumping step, making the vein visible by means of the imaging device.

The correct location of the collapsed vein segment can therefore be located and used in a subsequent step.

Preferably, the imaging step is performed during the collapsing step and the pumping step.

By doing this, the segment of the vein can be localized during collapsing, therefore defining a region of interest where the collapsed segment of the vein should be located and would become visible during the pumping step.

Preferably, compressing and releasing the vein during the pumping step is performed manually by an operator.

Alternatively, compressing and releasing the vein during the pumping step is performed with a compression device.

The compression device may be integrated in a device comprising the imaging device or may be a separated device such as a tourniquet.

Preferably, compressing and releasing the vein is repeated while the segment of the vein is fully or partially collapsed. This is done in order to correctly and reliably localize the collapsed vein segment.

Preferably, imaging is performed by at least one of colour Doppler imaging, pulsed wave Doppler imaging and B-mode ultrasound imaging.

Where colour Doppler imaging is used, the field of view (acquisition box) of the colour Doppler device is placed onto the region where the collapsed vein segment is expected. During the pumping step the blood forced to flow through the collapsed vein segment becomes therefore visible and the collapsed segment can be localized.

Where B-mode ultrasound imaging is used, the field of view of the colour Doppler device is placed onto the region where the collapsed vein segment is expected. During the pumping step the blood forced to flow through the collapsed vein segment changes the cross-section of the collapsed vein segment, and a hypoechoic spot corresponding to the open vein segment is visualized.

Where pulsed wave Doppler imaging is used, the measurement point is placed where the collapsed vein segment is expected and movement of the blood within the collapsed vein segment is detected.

Preferably, in particular when pulsed wave Doppler imaging is performed, the field of vision or the focus of the imaging device is displaced during the imaging step for localizing the vein. Displacement of the imaging device takes place while the pumping step is repeated until the collapsed vein segment moved by the forced blood flow is imaged by the imaging device.

According to a second alternative of the method, where a B-mode ultrasound imaging device with a main ultrasound propagation axis is used, the method comprises the following steps:

During a collapsing step, at least a segment of the vein to be localized is fully or partially collapsed at a collapsing site.

Collapsing of the vein is understood within the meaning of the present invention that the cross-section of the vein segment is reduced and/or the shape of the vein segment is changed.

Preferably, collapsing of the vein is performed by at least one of elevating at least the limb of the patient above a horizontal position, compressing the vein segment (e.g. with an inflatable balloon) and tumescence as cited above.

During an imaging step the collapsing site is visualized with the imaging device.

As cited above, the collapsed segment of the vein may be poorly visible or invisible.

In order to localize the collapsed segment of the vein, in a detecting step which is performed while the segment of the vein is fully or partially collapsed, at least one of the position and orientation of the imaging device is changed until a portion of the collapsed vein segment becomes hyperechoic, corresponding to a wall of the collapsed vein, preferably visualized on a display connected to the imaging device.

A hyperechoic spot is generated when the main ultrasound propagation axis is orthogonal to the vein wall. The position and/or orientation of the imaging device is therefore changed until the main propagation axis of the imaging device is orthogonal to the vein wall of the collapsed vein segment.

The collapsed vein segment can therefore be reliably localized.

Preferably, imaging of the collapsing site is performed during the collapsing step and the imaging step in order to determine a region of interest where the collapsed vein segment is expected.

Preferably, changing at least one of the position and orientation of the imaging device is performed manually by an operator.

Alternatively, changing at least one of the position and orientation of the imaging device is performed by a displacement device connected to the imaging device.

Preferably, at least one of the position and orientation of the imaging device is changed during the imaging step by moving the imaging device in at least one direction selected from: rotated around the main ultrasound propagation axis, rotated around an axis orthogonal to the main ultrasound propagation axis, displaced along a direction orthogonal to the main ultrasound propagation axis, preferably orthogonal to the imaging plane of the imaging device and displaced along a direction parallel to the main ultrasound propagation axis.

This is performed in order for an operator or for an image processing unit to differentiate between speckle and the vein and other structures of interest.

The movement range is preferably between 0.5 and 10 mm, in particular between 0.2 and 5 mm. The imaging device is preferably displaced with a maximum speed of 5 mm/s.

Where the imaging device is displaced along a direction orthogonal to the main ultrasound propagation axis, preferably orthogonal to the imaging plane of the imaging device, the direction is preferably chosen such that it is parallel to the direction of extension of the vein or parallel to the projection of the vein onto the skin if the vein is not parallel to the skin, wherein the imaging plane is preferably oriented as being orthogonal to the extension of the vein or orthogonal to the projection of the vein onto the skin if the vein is not parallel to the skin. The imaging device is then displaced in an oscillating manner and scans a sector of the collapsed vein.

Preferably the methods further comprise the steps of:

Targeting the focus of an HIFU device within the localized collapsing site during a targeting step and emitting at least one pulse of HIFU waves onto the targeted collapsing site with the HIFU device during a treatment step.

Preferably, the imaging device and the HIFU device are combined. In particular, if B-mode ultrasound imaging is used, the focus of the HIFU device lies within the imaging plane of the imaging device.

Preferably, the imaging device is rotated during the detecting step around an axis comprising the focus of the HIFU device.

This is done since the optimal position of the HIFU device may not the same as for the imaging device in order to correctly localize the collapsed vein segment. As cited before, the imaging device is displaced in order for the main ultrasound propagation axis to be orthogonal to the vein wall, making the vein wall visible as a hyperechoic spot. However, the optimal position for the HIFU device is with the skin orthogonal to the main propagation axis of the HIFU waves. Therefore the imaging device, in particular if integrated into the HIFU device, is moved around an axis comprising the focus of the HIFU device in order to keep the HIFU device focused onto the target. Of course, if it is determined that the focus of the HIFU device is not located within the collapsed vein segment, the focus of the HIFU device may be moved to the optimal position.

It is clear that after correctly targeting the HIFU device, the HIFU device may be moved to a position optimal for HIFU wave emission keeping the focus onto the localized collapsed vein segment.

Preferably, at least one of a diameter and the shape of the vein at the collapsing site is determined in a measurement step performed previously to the collapsing step, preferably with the patient in a standing position and wherein preferably a dose of thermal energy to be delivered during the treatment step is determined based on at least one of a diameter and the shape of the vein.

Preferably, a fluence value (the energy delivered to a surface of a cylinder) is determined based on the shape and/or diameter of the vein.

The invention further relates to a method for tumescence of vein within a limb, preferably within a leg, of a patient. The method is performed preferably according the methods described above.

A liquid is injected neighbouring a segment of the vein at a collapsing site such that the vein is not surrounded completely by the liquid, whereupon the segment of the vein closes.

As an example, if the vein is superficial, it may be pushed towards the deep fascia tissue. Since the boundary between the fascia filled with the liquid and the underlying tissue is easy to see with known imaging devices, in particular B-mode imaging, the operator has a good estimation of the collapsed vein segment location. Moreover, most of the advantages of a classical tumescence are kept: the distance to the skin is increased, the neighbouring sensitive structures can be protected and the patient pain is decreased. The sides of the vein where the liquid is injected are determined based on the presence of neighbouring sensitive structures to protect and the depth of the vein compared to the ideal treatment depth of the HIFU device.

The liquid preferably comprises an anesthetic active substance.

The liquid preferably comprises a normal saline solution.

Preferably a degassed liquid with a concentration of dissolved oxygen below 4 mg/L, preferably below 1 mg/L, is used to allow proper propagation of the HIFU waves.

The invention further relates to a degassed liquid for use in tumescence of a vein of a patient with a concentration of dissolved oxygen below 4 mg/L, preferably below 1 mg/L.

The preferred embodiments cited above with regard to the method also apply to the degassed liquid accordingly.

The invention further relates to a device for localizing and preferably visualizing a vein within a limb, preferably within a leg, of a patient.

The device is preferably adapted for performing the localizing methods cited above. Therefore, the descriptions of the methods also apply accordingly to such a device.

The device comprises an imaging device and compressing device for compressing and releasing the vein at a compression site located near the collapsing site, preferably distally of the collapsing site.

The device further comprises a control unit for controlling the imaging device and the compressing device, whereby the control unit is adapted to synchronize the imaging device to perform imaging of the compression site while the compression device compresses and releases the vein near the collapsing site.

Synchronizing of the imaging device and the compression device may be triggered by an operator or performed autonomously by the device, in particular based on predetermined parameters or parameters entered by the operator.

The control unit is preferably adapted to also control other systems of the device and synchronize them with the imaging device and compression device.

In particular, in case the imaging device is a colour Doppler or pulsed wave Doppler device, devices that may disturb imaging such as a cooling system of a balloon of an HIFU device are temporarily stopped for increasing image quality of the imaging device.

The invention further relates to a device for localizing and preferably visualizing a vein within a limb, preferably within a leg, of a patient.

The device is preferably adapted for performing the localizing methods cited above. Therefore, the descriptions of the methods also apply accordingly to such a device.

The device comprises an imaging device and a displacement device for displacing the imaging device relative to the patient.

Preferably, the displacement device is connected to the imaging device and allows displacement of the imaging device relative to the patient. Alternatively, the imaging device may be kept at a fixed position and the patient is displaced by means of the displacing device.

To follow, displacing the imaging device by the displacement device is therefore meant as displacing the imaging device relative to the patient and vice-versa.

The device further comprises a control unit adapted to synchronize the imaging device to perform imaging of a collapsing site of a vein segment while the imaging device is displaced by the displacement device.

The devices according to the present invention preferably comprise also an HIFU device.

In this case, the control unit is also adapted to control the HIFU device and in particular to focus the HIFU device onto the localized collapsed vein segment and to trigger the emission of at least one pulse of HIFU waves.

Where colour Doppler imaging is used, the field of view (acquisition box) of the colour Doppler device is placed onto the region where the collapsed vein segment is expected. During the pumping step the blood forced to flow through the collapsed vein segment becomes therefore visible and the collapsed segment can be localized.

Where B-mode ultrasound imaging is used, the field of view is placed onto the region where the collapsed vein segment is expected. During the pumping step the blood forced to flow through the collapsed vein segment changes the cross-section of the collapsed vein segment, and a hypoechoic spot corresponding to the open vein segment is visualized.

Where pulsed wave Doppler imaging is used, the measurement point is placed where the collapsed vein segment is expected and movement of the blood within the collapsed vein segment is detected.

Preferably, in particular when pulsed wave Doppler imaging is performed, the field of vision or the focus of the imaging device is displaced during the imaging step for localizing the vein. Displacement of the imaging device takes place while the pumping step is repeated until the collapsed vein segment moved by the forced blood flow is imaged by the imaging device.

The control unit is preferably adapted to automatically localize the collapsed vein segment by means of an image processing algorithm. Alternatively, the localization of the collapsed vein segment may be defined by a user by means of a graphical user interface.

The control unit is also preferably adapted to keep the focus of the HIFU device onto the localized collapsed vein segment when the imaging device is displaced.

Again, the control unit is also preferably adapted to control the displacement unit in order to change at least one of the position and orientation of the imaging device until a portion of the collapsed vein segment becomes hyperechoic, corresponding to a wall of the collapsed vein. This is preferably visualized on a display connected to the imaging device. Detection of the hyperechoic spot may be performed automatically by means of an image processing algorithm. Alternatively, the localization of the hyperechoic spot may be performed by a user by means of a graphical user interface Preferably, the displacement device is adapted to change at least one of the position and orientation of the imaging device while imaging is performed by moving the imaging device in at least one direction selected from: rotated around the main ultrasound propagation axis, rotated around an axis orthogonal to the main ultrasound propagation axis, displaced along a direction orthogonal to the main ultrasound propagation axis, preferably orthogonal to the imaging plane of the imaging device and displaced along a direction parallel to the main ultrasound propagation axis.

Where the imaging device is displaced along a direction orthogonal to the main ultrasound propagation axis, preferably orthogonal to the imaging plane of the imaging device, the direction is preferably chosen such that it is parallel to the direction of extension of the vein or parallel to the projection of the vein onto the skin if the vein is not parallel to the skin, wherein the imaging plane is preferably oriented as being orthogonal to the extension of the vein or orthogonal to the projection of the vein onto the skin if the vein is not parallel to the skin. The imaging device may be then displaced in an oscillating manner and to scan a sector of the collapsed vein.

This is performed in order for an operator or for an image processing unit to differentiate between speckle and the vein and other structures of interest.

The movement range is preferably between 0.5 and 10 mm, in particular between 0.2 and 5 mm. The imaging device is preferably displaced with a maximum speed of 5 mm/s.

Alternatively, the displacement device may be adapted to only limit the movement to a maximum range and/or limit the direction of movement/rotation as cited above, whereby the imaging device is then displaced manually by an operator.

Preferably, the imaging device is rotated during the detecting step around an axis comprising the focus of the HIFU device.

It is clear that after correctly targeting the HIFU device, the HIFU device may be moved to a position optimal for HIFU wave emission keeping the focus onto the localized collapsed vein segment.

The control unit is preferably adapted to control the displacement unit and the HIFU device according to a predetermined treatment plan, wherein after at least one pulse of HIFU waves focused onto a first target location within the collapsed vein segment has been emitted, the imaging device and the HIFU device are automatically displaced to a second target location within the collapsed vein segment and emission of HIFU waves is triggered. Of course, before treating the second target location, localization of the collapsed vein segment may be performed as described above in order to confirm the correct localization of the collapsed vein segment performed in the previous step(s).

The invention further relates to a method of occluding a vein within a limb, preferably within a leg, of a patient, with an HIFU device.

As cited above, HIFU waves may be used to treat a vein in a non-invasive manner and induce occlusion of the vein by thermal and/or cavitation effects on the vein wall.

In a collapsing step, at least a segment of the vein to be localized is fully or partially collapsed at a collapsing site.

This step is performed as cited above with regard to the other methods/devices of the present invention.

In an imaging step, the collapsing site is localized with an imaging device.

The imaging step is performed as cited above with regard to the other methods/devices of the present invention.

In some cases, depending on the circumstances such as the dimensions of the vein, the shape of the vein or the used imaging method, the collapsed vein segment may be localized without the need of performing the above mentioned pumping step or detecting step.

Therefore, the collapsed vein segment may be localized.

In a targeting step, the focus of the HIFU device is targeted within the localized collapsing site during a targeting step.

In a treatment step, at least one pulse of HIFU waves is emitted onto the targeted collapsing site with the HIFU device.

It is clear from the above that the particular description of the method/devices previously described in the present invention also applies accordingly to the method of occluding a vein and to a device for occluding the vein.

In particular, the steps may be repeated along the collapsed vein segment in order to treat the vein over a given length.

The imaging device can also be moved as described previously in order to scan the collapsed vein segment and in particular improve imaging of the collapsed vein segment by discriminating between image artefacts such as speckle and the collapsed vein segment.

Figure 2:
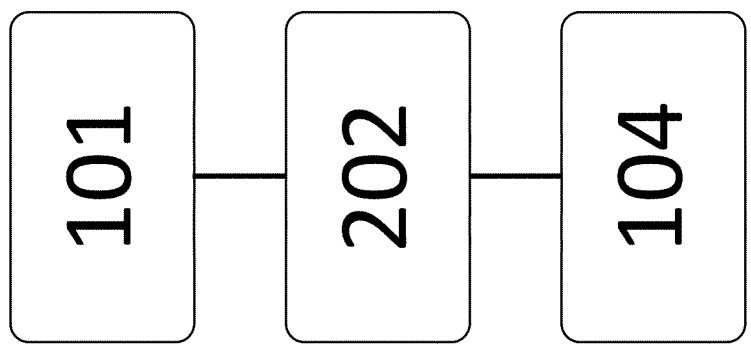
Figure 3:
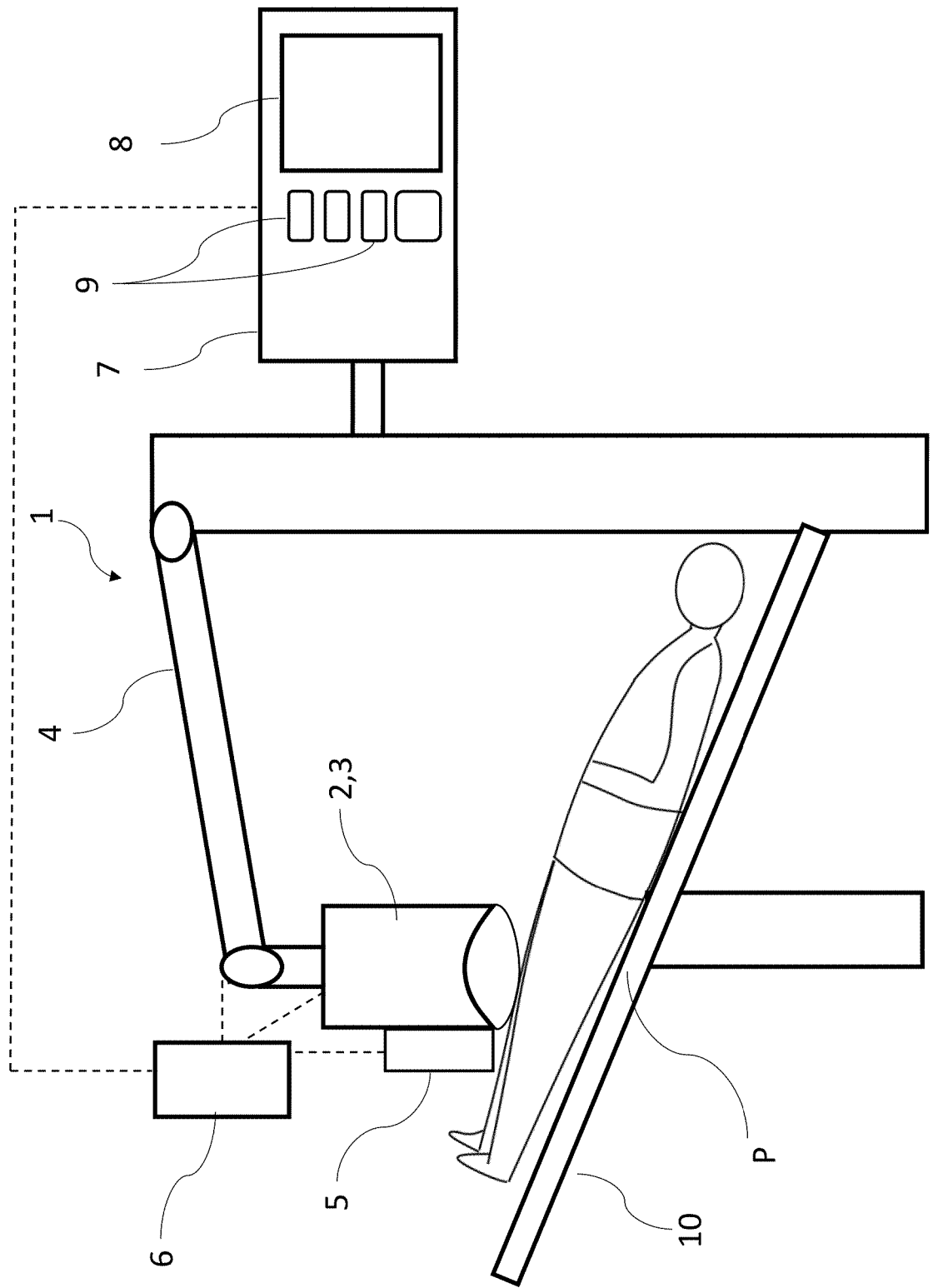

The invention will now be described in more detail by way of non-limiting, exemplary embodiments in connection with the drawings which show:

FIG. 1 a flow chart according to a first alternative of the method according to the present invention;

FIG. 2 a flow chart according to a second alternative of the method according to the present invention; and FIG. 3 a schematic arrangement of a device according to the present invention.

FIG. 1 shows a first alternative of the method according to the present invention. In a first collapsing step 101, at least a segment of the targeted vein is collapsed. As cited above, the vein may be collapsed by inclining the limb of the patient or by tumescence.

In order to reliably localize the collapsed segment of the vein with an imaging device, blood flow is forced into the collapsed vein segment in a pumping step 102. If the pumping step 102 is performed by compressing/releasing the vein, the compression is preferably performed upstream of the collapsed segment, either manually by an operator or with a compression device. A temporary blood flow is therefore forced through the collapsed segment of the vein, making the collapsed segment visible by means of the imaging device during an imaging step 103.

In the case where colour Doppler is used as imaging method, the blood flow becomes clearly visible. If B-mode ultrasound imaging is used, the blood flow causes opening and closing of the collapsed vein segment. The vein lumen therefore appears as a hypoechoic spot (corresponding to the vein lumen opening and closing). As an alternative, pulsed wave Doppler can also be used as an imaging step. The measurement location of the pulsed wave Doppler device is placed in the region where the collapsed segment is expected and the pumping step 102 is performed. If a signal is detected by means of the pulsed wave Doppler during the imaging step 103, then the pulsed wave Doppler device has been correctly focused onto the collapsed segment of the vein. Otherwise, the measurement location is shifted and the pumping step 102 is repeated until the location of the collapsed vein segment has been correctly determined in the imaging step 103.

After the correct location of the collapsed vein segment has been determined, a treatment step 104 may be performed. An HIFU device is focused onto the collapsed vein segment and a pulse or a series of pulses of HIFU waves is emitted in order to treat the collapsed vein segment and occlude it.

As may be seen from FIG. 2, where an alternative of the method according to the present invention is shown, the collapsing step 101 is first performed.

Instead of the pumping step 102, a detection step 202 is then performed. During the detection step 202, imaging of the region of interest around the collapsed vein segment is performed by means of B-mode ultrasound imaging.

The B-mode ultrasound imaging device has a main ultrasound propagation axis. During the detection step 202, the imaging device is moved until a hyperechoic spot corresponding to the vein wall of the collapsed vein segment is detected and the location of the collapsed vein segment has been correctly determined.

Also in this case, the treatment step 104, as described with regard to FIG. 1, may be performed after the detection step 202.

The HIFU device and the B-mode imaging device are preferably a combined device where the focus of the HIFU device lies in the imaging plane of the imaging device.

In this case, the displacement of the B-mode imaging device also implicitly causes a displacement of the HIFU device. If the vein does not run parallel to the skin, the HIFU device would not be in the optimal position for emitting the HIFU waves (where the HIFU waves beam is orthogonal to the skin surface to enhance HIFU waves transmission through the skin). In this case, after the detection step 202 has been performed and the correct location of the region to be treated has been determined, the combined B-mode imaging device and HIFU device is displaced to an optimal position for the emission of HIFU waves, while the focus of the HIFU device is positioned onto the region to be treated. Thus, there are two different positions/angles, one which is optimal for visualization (e.g. with the main ultrasound propagation axis orthogonal to the wall of the collapsed vein segment and one which is optimal for delivering HIFU energy (e.g. with the main propagation axis of the HIFU waves orthogonal to the skin).

Where the combined B-mode imaging device and HIFU device is displaced by means of a device, e.g. a robotic arm, the device may comprise a control unit designed to move the combined B-mode imaging device and HIFU device correctly. The correct location of the region to be treated may in this case be defined by a user or detected automatically by an image processing algorithm of an image processing unit connected to the control unit.

FIG. 3 shows a device 1 according to the present invention. The device 1 comprises a treatment head comprising an HIFU device 2 and an imaging device 3. The treatment head is mounted on a robot arm 4. Adjacent to the treatment head there is located a compression device 5. The device 1 further comprises a control unit 6 connected (schematically represented by the dotted lines) to the HIFU device 2, the imaging device 3, the robot arm 4, the compression device 5 and a user interface 7.

The user interface 7 comprises a display 8 and a plurality of switches 9 for manually controlling the device 1.

A patient P is lying on an inclined table 10, the vein to be targeted has therefore been collapsed.

The control unit 6 is adapted to control the HIFU device 2, the imaging device 3, the movement of the robot arm 4 and the compression device 5 in order to perform the methods as cited above. In addition, the user can control the operation of the device 1 by means of the user interface 7. The display 8 displays, among other information, the images generated by the imaging device 3. The switches 9 are used for triggering different functions of the device 1, in particular to switch to different operating modes, to trigger emission of HIFU waves by the HIFU device 2 (if this is not performed automatically by the device 1), move the treatment head by means of the robot arm 4 etc.

As an example, where the device 1 is adapted to perform the method described with reference to FIG. 1, the control unit 1 controls the synchronization of the imaging device 2 and the compression device 5 while the pumping step 102 and the imaging step 103 are performed. The correct localization of the collapsed vein segment is therefore possible. After the collapsed vein segment has been localized, the control unit 1 controls the correct focusing of the HIFU device 2 onto the collapsed vein segments and the triggering of the emission of the HIFU waves.

In the case the method described with reference to FIG. 2 is performed, the control unit 1 synchronizes the movement of the treatment head and therefore of the imaging device 3 in order to orient the imaging device 3 until the hyperechoic spot corresponding to the collapsed vein segment wall has been correctly localized. In addition, the control unit 1 then controls correct positioning of the focused HIFU device 2 for optimal emission of the HIFU waves. Preferably, the control unit 1 also controls the movement of the treatment head by means of the robot arm 4 when scanning of the vein as described above is performed.

The invention claimed is:

1. A method of localizing a vein within a limb of a patient, with an imaging device selected from a color Doppler imaging device, a pulsed wave Doppler imaging device, and a B-mode ultrasound imaging device, the method comprising the steps of:
    a. collapsing at least a segment of the vein to be localized at a collapsing site during a collapsing step such as to stop blood flow, such that the segment of the vein becomes invisible by B-mode imaging and/or Doppler imaging;
    b. inducing blood flow within the vein at the collapsing site, during a pumping step, while the segment of the vein is collapsed; and
    c. visualizing the collapsing site with the imaging device, during an imaging step, at least during the pumping step, and detecting the presence of the collapsed segment by detecting one of
        i. the induced blood flow by means of color Doppler imaging,
        ii. a signal of the pulsed wave Doppler imaging device, and
        iii. a hypoechoic spot by means of B-mode ultrasound imaging.

2. The method according to claim 1, wherein the imaging step is performed during the collapsing step and the pumping step.

3. The method according to claim 1, wherein compressing and releasing the vein, during the pumping step, is performed manually.

4. The method according to claim 1, wherein compressing and releasing the vein, during the pumping step, is performed with a non-manual compression device.

5. The method according to claim 1, wherein compressing and releasing the vein is repeated while the segment of the vein is fully or partially collapsed.

6. The method according to claim 1, wherein a field of vision or a focus of the imaging device is displaced, during the imaging step, for localizing the collapsed segment of the vein.

7. A method of occluding a vein within a limb with an HIFU device, the method comprising the steps of:
   a. localizing at least a segment of the vein at a collapsing site using the method of claim 1;
   b. targeting a focus of the HIFU device within the localized collapsing site during a targeting step; and
   c. emitting at least one pulse of HIFU waves onto the targeted collapsing site with the HIFU device during a treatment step.

8. The method according to claim 1, further comprising a step of:
   d. targeting the focus of an HIFU device within the localized collapsing site during a targeting step;
   e. emitting at least one pulse of HIFU waves onto the targeted collapsing site with the HIFU device during a treatment step.

9. The method according to claim 1, wherein at least one of a diameter and a shape of the vein, at the collapsing site, is determined in a measurement step performed prior to the collapsing step.

10. The method according to claim 1, wherein collapsing of the vein is performed by at least one of elevating at least the limb of the patient above a horizontal position, and compressing the vein segment and tumescence.

11. The method according to claim 10, wherein the imaging of the collapsing site is also performed during the collapsing step.

* * * * *